(12) United States Patent
Li et al.

(10) Patent No.: US 7,972,624 B2
(45) Date of Patent: Jul. 5, 2011

(54) METHOD OF MANUFACTURING MODIFIED RELEASE DOSAGE FORMS

(76) Inventors: Shun-Por Li, Lansdale, PA (US); Harry S. Sowden, Glenside, PA (US); David Wynn, Huntington Valley, PA (US); Der-Yang Lee, Flemington, NJ (US); Martin Thomas, Lake Worth, FL (US)

( * ) Notice: Subject to any disclaimer, the term of this patent is extended or adjusted under 35 U.S.C. 154(b) by 0 days.

(21) Appl. No.: 12/391,475

(22) Filed: Feb. 24, 2009

(65) Prior Publication Data

US 2009/0155372 A1    Jun. 18, 2009

Related U.S. Application Data (63) Continuation of application No. 10/477,334, filed as application No. PCT/US02/31022 on Sep. 28, 2002, which is a continuation-in-part of application No. 09/966,939, filed on Sep. 28, 2001, now Pat. No. 6,837,696, which is a continuation-in-part of application No. 09/966,450, filed on Sep. 28, 2001, now Pat. No. 6,982,094, which is a continuation-in-part of application No. 09/966,509, filed on Sep. 28, 2001, now Pat. No. 6,767,200, which is a continuation-in-part of application No. 09/966,497, filed on Sep. 28, 2001, now Pat. No. 7,122,143, which is a continuation-in-part of application No. 09/966,414, filed on Sep. 28, 2001, now abandoned.

(51) Int. Cl.
  *A61K 9/22* (2006.01)
  *A23G 3/02* (2006.01)
(52) U.S. Cl. .......................... 424/468; 426/512
(58) Field of Classification Search .................. None
  See application file for complete search history.

(56) References Cited

U.S. PATENT DOCUMENTS

| | | |
|---|---|---|
| 582,438 A | 5/1897 | Scheidler |
| 599,865 A | 3/1898 | Richards |
| 2,307,371 A | 1/1943 | Hileman |
| 2,996,431 A | 8/1961 | Barry |
| 3,085,942 A | 4/1963 | Magid et al. |
| 4,139,627 A | 4/1963 | Magid et al. |
| 3,146,169 A | 8/1964 | Stephenson et al. |
| 3,185,626 A | 5/1965 | Baker |
| 3,279,995 A | 10/1968 | Reid |
| 3,627,582 A | 12/1971 | Troy et al. |
| 3,627,583 A | 12/1971 | Troy et al. |
| 3,670,065 A | 6/1972 | Eriksson et al. |
| 3,726,622 A | 4/1973 | DeTroyer et al. |
| 3,760,804 A | 9/1973 | Higuchi et al. |
| 3,804,570 A | 4/1974 | Hoschele et al. |
| 3,832,252 A | 8/1974 | Higuchi et al. |
| 3,851,638 A | 12/1974 | Alexander |
| 4,076,819 A | 2/1978 | Maffrand |
| 4,097,606 A | 6/1978 | Chavkin et al. |
| 4,111,202 A | 9/1978 | Theeuwes |
| 4,139,589 A | 2/1979 | Beringer et al. |
| 4,173,626 A | 11/1979 | Dempski et al. |
| 4,198,390 A | 4/1980 | Rider |
| 4,218,433 A | 8/1980 | Kooichi et al. |
| 4,230,693 A | 10/1980 | Izzo et al. |
| 4,271,206 A | 6/1981 | Fariel et al. |
| 4,273,793 A | 6/1981 | Fariel et al. |
| 4,279,926 A | 7/1981 | Bruzzese et al. |
| 4,292,017 A | 9/1981 | Doepel |
| 4,322,449 A | 3/1982 | Voss et al. |
| 4,362,757 A | 12/1982 | Chen et al. |
| 4,371,516 A | 2/1983 | Gregory et al. |
| 4,372,942 A | 2/1983 | Cimiluca |
| 4,392,493 A | 7/1983 | Niemeijer |
| 4,425,332 A | 1/1984 | James |
| 4,449,983 A | 5/1984 | Cortese et al. |
| 4,473,526 A | 9/1984 | Buhler et al. |
| RE31,764 E | 12/1984 | Voss et al. |
| 4,517,205 A | 5/1985 | Aldrich |
| 4,518,335 A | 5/1985 | Pujari |
| 4,528,335 A | 7/1985 | Selby et al. |

(Continued)

FOREIGN PATENT DOCUMENTS

CN        1099262 A        1/1995

(Continued)

OTHER PUBLICATIONS

Carbowax supplement (Dow Chemical); p. 18, Table 2.*
Catellani, P.L. et al., "Centrifugal die filling system in a new rotary tablet machine", International Journal of Pharmaceutics, 88 (1992), pp. 285-291.
Cuff, George et al., "A Preliminary Evaluation of Injection Moldign as a Technology to Produce Tablets", Pharmaceutical Technology (1998), Jun. 1998, pp. 96-106.

(Continued)

*Primary Examiner* — Robert A Wax
*Assistant Examiner* — Jeffrey Palenik
(74) *Attorney, Agent, or Firm* — Laura Donnelly (57) ABSTRACT

In one embodiment a dosage form comprises at least one active ingredient and a molded matrix which comprises 10-100% of a material having a melting point of less than about 100 degrees C. selected from the stamp consisting of thermoplastic polyalkylene oxides, low melting hydrophobic materials, thermoplastic polymers, thermoplastic starches and combinations thereof, and the matrix is capable of providing modified release of the active ingredient upon contacting of the dosage form with a liquid medium. The dosage form may additionally comprise uncoated particles which may contain at least one active ingredient. In another embodiment, a dosage form comprises at least one active ingredient, a plurality of particles and a molded matrix, wherein at least a portion of the particles are coated. The coated particles, the matrix or both may comprise at least one active ingredient, and the coated particles or the matrix or a combination thereof is capable of providing modified release of the active ingredient upon contacting of the dosage form with a liquid medium.

14 Claims, 2 Drawing Sheets

U.S. PATENT DOCUMENTS

| | | |
|---|---|---|
| 4,533,345 A | 8/1985 | Louw |
| 4,543,370 A | 9/1985 | Porter et al. |
| 4,544,345 A | 10/1985 | Buhler et al. |
| 4,564,525 A | 1/1986 | Mitchell et al. |
| 4,569,650 A | 2/1986 | Kramer |
| 4,576,604 A | 3/1986 | Guittard et al. |
| 4,610,884 A | 9/1986 | Lewis et al. |
| 4,643,894 A | 2/1987 | Porter et al. |
| 4,661,521 A | 4/1987 | Salpekar et al. |
| 4,663,147 A | 5/1987 | DePrince |
| 4,683,256 A | 7/1987 | Porter et al. |
| 4,686,212 A | 8/1987 | Ducatman et al. |
| 4,725,441 A | 2/1988 | Porter et al. |
| 4,749,575 A | 6/1988 | Rotman |
| 4,757,090 A | 7/1988 | Salpekar et al. |
| 4,762,719 A | 8/1988 | Forester |
| 4,781,714 A | 11/1988 | Eckenhoff et al. |
| 4,786,505 A | 11/1988 | Lovgren et al. |
| 4,801,461 A | 1/1989 | Hamel et al. |
| 4,802,924 A | 2/1989 | Woznicki et al. |
| 4,803,076 A | 2/1989 | Ranade |
| 4,813,818 A | 3/1989 | Samzone |
| 4,816,262 A | 3/1989 | McMullen |
| 4,820,524 A | 4/1989 | Berta |
| 4,828,841 A | 5/1989 | Porter et al. |
| 4,851,226 A | 7/1989 | Julian et al. |
| 4,853,230 A | 8/1989 | Lovgren et al. |
| 4,857,330 A | 8/1989 | Stephens et al. |
| 4,863,742 A | 9/1989 | Panoz et al. |
| 4,865,849 A | 9/1989 | Conte et al. |
| 4,873,231 A | 10/1989 | Smith |
| 4,882,167 A | 11/1989 | Jang |
| 4,894,236 A | 1/1990 | Jang |
| 4,906,478 A | 3/1990 | Valentine et al. |
| 4,929,446 A | 5/1990 | Bartolucci |
| 4,965,027 A | 10/1990 | Takahashi |
| 4,978,483 A | 12/1990 | Redding, Jr. |
| 4,980,169 A | 12/1990 | Oppenheimer et al. |
| 4,980,170 A | 12/1990 | Schneider et al. |
| 4,983,394 A | 1/1991 | Hussein et al. |
| 4,984,240 A | 1/1991 | Keren-Zvi et al. |
| 4,999,226 A | 3/1991 | Schock et al. |
| 5,002,970 A | 3/1991 | Eby, III |
| 5,004,614 A | 4/1991 | Staniforth |
| 5,032,406 A | 7/1991 | Dansereau et al. |
| 5,059,112 A | 10/1991 | Wieser |
| 5,075,114 A | 12/1991 | Roche |
| 5,089,270 A | 2/1992 | Hampton |
| 5,133,892 A | 7/1992 | Chun et al. |
| 5,145,868 A | 9/1992 | von Sprecher et al. |
| 5,146,730 A | 9/1992 | Sadek et al. |
| 5,169,645 A | 12/1992 | Shukla et al. |
| 5,188,840 A | 2/1993 | Iida et al. |
| 5,200,191 A | 4/1993 | Steele et al. |
| 5,200,193 A | 4/1993 | Radebaugh et al. |
| 5,213,738 A | 5/1993 | Hampton et al. |
| 5,213,808 A | 5/1993 | Ba-Shalom et al. |
| 5,228,916 A | 7/1993 | Berta |
| 5,229,164 A | 7/1993 | Pins et al. |
| 5,232,706 A | 8/1993 | Palomo Coll |
| 5,275,822 A | 1/1994 | Valentine et al. |
| 5,286,497 A | 2/1994 | Hendrickson et al. |
| 5,368,863 A | 11/1994 | Eckenhoff et al. |
| 5,375,963 A | 12/1994 | Repka et al. |
| 5,391,378 A | 2/1995 | Sanderson |
| 5,393,533 A | 2/1995 | Versic |
| 5,405,617 A | 4/1995 | Gowan, Jr. et al. |
| 5,405,642 A | 4/1995 | Gilis et al. |
| 5,407,686 A | 4/1995 | Patel et al. |
| 5,415,868 A | 5/1995 | Smith et al. |
| 5,424,075 A | 6/1995 | Daher et al. |
| 5,427,614 A | 6/1995 | Wittwer et al. |
| 5,433,951 A | 7/1995 | Serajuddin et al. |
| 5,436,026 A | 7/1995 | Berta |
| 5,456,920 A | 10/1995 | Matoba et al. |
| 5,459,983 A | 10/1995 | Sadek et al. |
| 5,462,747 A | 10/1995 | Radebaugh et al. |
| 5,464,631 A | 11/1995 | Hoover et al. |
| 5,464,633 A | 11/1995 | Conte et al. |
| 5,489,436 A | 2/1996 | Hoy et al. |
| 5,510,385 A | 4/1996 | Stroppolo et al. |
| 5,511,361 A | 4/1996 | Sauter |
| 5,538,125 A | 7/1996 | Berta |
| 5,558,879 A | 9/1996 | Chen |
| 5,559,110 A | 9/1996 | Aungst |
| 5,578,336 A | 11/1996 | Monte |
| 5,593,696 A | 1/1997 | McNally et al. |
| 5,609,010 A | 3/1997 | Sauter |
| 5,610,214 A | 3/1997 | Olson |
| 5,614,207 A | 3/1997 | Shah et al. |
| 5,626,875 A | 5/1997 | Ballester Rodes et al. |
| 5,627,971 A | 5/1997 | Miernik |
| 5,630,871 A | 5/1997 | Jordan |
| 5,641,536 A | 6/1997 | Lech et al. |
| 5,654,005 A | 8/1997 | Chen et al. |
| 5,658,589 A | 8/1997 | Parekh et al. |
| 5,679,406 A | 10/1997 | Berta |
| 5,681,584 A | 10/1997 | Savastano et al. |
| 5,683,719 A | 11/1997 | Newton |
| 5,711,961 A | 1/1998 | Reiner et al. |
| 5,738,874 A | 4/1998 | Conte et al. |
| 5,753,265 A | 5/1998 | Bergstrand et al. |
| 5,795,588 A | 8/1998 | Sauter |
| 5,807,579 A | 9/1998 | Vilkov et al. |
| 5,807,580 A | 9/1998 | Luber |
| 5,817,338 A | 10/1998 | Bergstrand et al. |
| 5,824,338 A | 10/1998 | Jacobs et al. |
| 5,827,535 A | 10/1998 | Stone |
| 5,827,874 A | 10/1998 | Meyer et al. |
| 5,830,501 A | 11/1998 | Dong et al. |
| 5,830,502 A * | 11/1998 | Dong et al. .................. 424/473 |
| 5,834,035 A | 11/1998 | Osada et al. |
| 5,837,301 A | 11/1998 | Arnott et al. |
| 5,849,327 A | 12/1998 | Berliner et al. |
| 5,853,760 A | 12/1998 | Cremer |
| 5,861,173 A | 1/1999 | Nishioka et al. |
| 5,871,781 A | 2/1999 | Myers et al. |
| 5,912,013 A | 6/1999 | Rudnic et al. |
| 5,942,034 A | 8/1999 | Brehant et al. |
| 5,980,944 A | 11/1999 | Stevens et al. |
| 5,997,903 A | 12/1999 | Dietrich et al. |
| 5,997,905 A | 12/1999 | McTeigue et al. |
| 6,001,391 A | 12/1999 | Zeidler et al. |
| 6,013,281 A | 1/2000 | Lundberg et al. |
| 6,022,554 A | 2/2000 | Lee et al. |
| 6,077,541 A | 6/2000 | Chen et al. |
| 6,090,401 A | 7/2000 | Gowan et al. |
| 6,096,340 A | 8/2000 | Chen et al. |
| 6,103,257 A | 8/2000 | Nisonoff |
| 6,103,260 A | 8/2000 | Luber et al. |
| 6,110,499 A | 8/2000 | Shivanand et al. |
| 6,110,500 A | 8/2000 | Kim |
| 6,117,479 A | 9/2000 | Hogan et al. |
| 6,120,802 A | 9/2000 | Breitenbach et al. |
| 6,123,861 A | 9/2000 | Santini et al. |
| 6,149,939 A | 11/2000 | Strumor et al. |
| 6,149,943 A | 11/2000 | McTeigue et al. |
| 6,159,499 A | 12/2000 | Seth |
| 6,174,548 B1 | 1/2001 | Chen et al. |
| 6,183,776 B1 | 2/2001 | Depui et al. |
| 6,200,590 B1 | 3/2001 | Eley |
| 6,207,198 B1 | 3/2001 | Seth |
| 6,217,902 B1 | 4/2001 | Tanner et al. |
| 6,224,910 B1 | 5/2001 | Ullah et al. |
| 6,248,355 B1 | 6/2001 | Seth |
| 6,248,361 B1 | 6/2001 | Johnson et al. |
| 6,248,760 B1 | 6/2001 | Wilhelmsen |
| 6,264,985 B1 | 7/2001 | Cremer |
| 6,270,805 B1 | 8/2001 | Chen et al. |
| 6,274,162 B1 | 8/2001 | Steffenino et al. |
| 6,294,200 B1 | 9/2001 | Conte et al. |
| 6,322,819 B1 | 11/2001 | Burnside et al. |
| 6,331,316 B1 | 12/2001 | Ullah et al. |
| 6,350,398 B1 | 2/2002 | Breitenbach et al. |
| 6,365,185 B1 | 4/2002 | Ritschel |
| 6,372,252 B1 | 4/2002 | Blume et al. |
| 6,394,094 B1 | 5/2002 | McKenna et al. |

| | | | |
|---|---|---|---|
| 6,428,810 B1 | 8/2002 | Bergstrand et al. | |
| 6,489,346 B1 | 12/2002 | Phillips | |
| 6,555,139 B2 | 4/2003 | Sharma | |
| 6,569,457 B2 | 5/2003 | Ullah et al. | |
| 6,602,522 B1 | 8/2003 | Chen et al. | |
| 6,613,354 B2 | 9/2003 | Depui et al. | |
| 6,726,927 B2 | 4/2004 | Chen | |
| 6,730,646 B1 | 5/2004 | Waschenbach et al. | |
| 6,742,646 B2 | 6/2004 | Sowden et al. | |
| 6,727,200 B2 | 7/2004 | Sowden et al. | |
| 6,767,200 B2 | 7/2004 | Sowden et al. | |
| 6,837,696 B2 | 1/2005 | Sowden et al. | |
| 6,982,094 B2 | 1/2006 | Sowden | |
| 7,122,143 B2 | 10/2006 | Sowden et al. | |
| 2001/0001280 A1 | 5/2001 | Dong et al. | |
| 2002/0028240 A1 | 3/2002 | Sawada et al. | |
| 2002/0051807 A1 | 5/2002 | Faour et al. | |
| 2002/0082299 A1 | 6/2002 | Meyer | |
| 2003/0059466 A1 | 3/2003 | Seth | |
| 2003/0060393 A1 | 3/2003 | Waschenbach et al. | |
| 2003/0066068 A1 | 4/2003 | Srinivas | |
| 2003/0068367 A1 | 4/2003 | Sowden et al. | |
| 2003/0068373 A1 | 4/2003 | Luber et al. | |
| 2003/0070903 A1 | 4/2003 | Sowden | |
| 2003/0072799 A1 | 4/2003 | Sowden et al. | |
| 2003/0086973 A1 | 5/2003 | Sowden et al. | |
| 2003/0124183 A1 | 7/2003 | Sowden et al. | |
| 2003/0190362 A1 | 10/2003 | Sackler et al. | |
| 2003/0232082 A1 | 12/2003 | Li et al. | |
| 2003/0235616 A1 | 12/2003 | Sowden et al. | |
| 2005/0074514 A1 | 4/2005 | Anderson | |

FOREIGN PATENT DOCUMENTS

| | | |
|---|---|---|
| CN | 1130867 A | 9/1996 |
| CN | 1183047 A | 5/1998 |
| DE | 27 10 307 | 9/1977 |
| DE | 3629994 A1 | 3/1988 |
| DE | 198 34 180 A1 | 2/2000 |
| DE | 19925710 | 12/2000 |
| DE | 199 54 420 A1 | 5/2001 |
| DE | 199 63 569 A1 | 7/2001 |
| EP | 0 088 556 B1 | 9/1983 |
| EP | 60023 B1 | 8/1984 |
| EP | 237200 B1 | 2/1987 |
| EP | 0 239 983 B1 | 10/1987 |
| EP | 239983 B1 | 10/1987 |
| EP | 325492 A1 | 7/1989 |
| EP | 0 387 885 B1 | 9/1990 |
| EP | 0 455 599 A1 | 11/1991 |
| EP | 0 294 993 B1 | 12/1991 |
| EP | 0 861 659 A1 | 2/1992 |
| EP | 0 481 547 A1 | 4/1992 |
| EP | 0 531 524 B1 | 3/1993 |
| EP | 0 572 731 A1 | 12/1993 |
| EP | 0 646 650 A2 | 4/1995 |
| EP | 0 788 790 A2 | 2/1996 |
| EP | 496437 B1 | 7/1996 |
| EP | 0 740 938 B1 | 11/1996 |
| EP | 0 864 324 B1 | 3/1997 |
| EP | 519144 B1 | 8/1997 |
| EP | 0 619 854 B1 | 3/1998 |
| EP | 0 834 516 B1 | 4/1998 |
| EP | 861659 A | 9/1998 |
| EP | 0 950 402 B1 | 2/1999 |
| EP | 1 029 892 B1 | 8/2000 |
| EP | 1 077 065 A1 | 2/2001 |
| EP | 1138661 A1 | 10/2001 |
| FR | 2 011 960 | 3/1970 |
| FR | 2 604 904 A1 | 4/1988 |
| GB | 866 681 | 4/1961 |
| GB | 994 742 | 5/1961 |
| GB | 888 038 | 1/1962 |
| GB | 936 386 | 9/1963 |
| GB | 1 144 915 | 3/1969 |
| GB | 1372040 | 12/1971 |
| GB | 1 372 040 | 10/1974 |
| GB | 1 464 388 | 2/1977 |
| GB | 1510772 | 5/1978 |
| GB | 759081 | 10/1986 |
| GB | 2 197 778 A | 6/1988 |
| GB | 2 284 760 A | 6/1995 |
| JP | 63-10719 | 1/1988 |
| JP | SHO B1 (1986) 125691 | 5/1988 |
| JP | HEI 3 (1991) 232815 | 10/1991 |
| JP | HEI 5 (1993) 345721 | 12/1993 |
| JP | 7-242535 | 9/1995 |
| NL | 86 02 556 | 5/1988 |
| WO | WO 89/11968 | 12/1989 |
| WO | WO 92/22284 A | 12/1992 |
| WO | WO 94/06416 A1 | 3/1994 |
| WO | WO 94/07470 A1 | 4/1994 |
| WO | WO 95/02396 * | 1/1995 |
| WO | WO 95/02396 A1 | 1/1995 |
| WO | WO 95/15156 A1 | 6/1995 |
| WO | WO 97/06695 A1 | 2/1997 |
| WO | WO 97/15293 A2 | 5/1997 |
| WO | WO 97/49384 | 12/1997 |
| WO | WO 98/20870 A1 | 5/1998 |
| WO | WO 99/02136 A1 | 1/1999 |
| WO | WO 99/6157 | 2/1999 |
| WO | WO 99/32092 A1 | 7/1999 |
| WO | WO 99/51209 A1 | 10/1999 |
| WO | WO 99/56730 A1 | 11/1999 |
| WO | WO 99/62496 A1 | 12/1999 |
| WO | WO 00/18447 A2 | 4/2000 |
| WO | WO 00/25755 A1 | 5/2000 |
| WO | WO 01/28558 | 4/2001 |
| WO | WO 01/49815 A2 | 7/2001 |
| WO | WO 01/58433 | 8/2001 |
| WO | WO 01/85437 A1 | 11/2001 |
| WO | WO 02/11702 A2 | 2/2002 |
| WO | WO 02/19833 A2 | 3/2002 |
| WO | WO 03/007917 | 1/2003 |
| WO | WO 03/026626 A | 4/2003 |
| WO | WO 03/028620 A | 4/2003 |
| WO | WO 03/063840 A2 | 8/2003 |
| WO | WO 03/080026 A | 10/2003 |
| WO | WO 2004/010978 A | 2/2004 |
| WO | WO 2004/066982 A | 8/2004 |
| WO | WO 2004/112756 A | 12/2004 |
| WO | WO 2006/047493 A | 5/2006 |

OTHER PUBLICATIONS

Lachman, Leon et al., "Chapter II—Tablets", The Theory and Practice of Industrial Pharmacy, (1986), pp. 293-345.
International Search Report dated Feb. 26, 2003 for PCT/US02/31022.
International Search Report dated Mar. 3, 2003 for PCT/US02/31117.
International Search Report dated Feb. 20, 2003 for PCT/US02/31115.
International Search Report dated Feb. 20, 2003 for PCT/US02/31164.
International Search Report dated Jan. 8, 2004 for PCT/US03/08891.
International Search Report dated Feb. 11, 2003 for PCT/US02/31024.
International Search Report dated Feb. 6, 2003 for PCT/US02/31163.
European Search Report EP05253780 dated Aug. 2006.
Ceschel, G.C., et al., "Sugar Coating of Tablets", Bollettino Chimico Farmaceutico, 1980, pp. 127-134, vol. 119, Milan Italy.
Cobby, John et al., "Influence of Shape Factors on Kinetics of Drug Release from Matrix Tablets I: Theoretical". Journal of Pharmaceutical Sciences, May 1974, vol. 63, No. 5, pp. 725-732.
Cobby, John et al., "Influence of Shape Factors on Kinetics of Drug Release from Matrix Tablets II: Experimental". Journal of Pharmaceutical Sciences, May 1974, vol. 63, No. 5, pp. 732-737.
Cleave, J.P., "Some geometrical considerations concerning the design of tables". J. Pharm. Pharmacol, 1965, pp. 698-702.
Edwards, W.P.P., "Pan Coating". The Science of Sugar Confectionery, 2000, pp. 95-100, 1st Edition, The Royal Society of Chemistry, London, England.
Desai, S.J. et al., "Investigation of Factors Influencing Release of Solid Drug Dispersed in Inert Matrices". Journal of Pharmaceutical Sciences, Oct. 1965, vol. 54, No. 10, pp. 1459-1464.

"Electrostatics in Continuous Tablet Coating", Manufacturing Chemist, Oct. 1998, vol. 69, No. 10. pp. 13-16.

Eith, L., et al., "Injection-Moulded Drug-Delivery Systems", Manufacturing Chemist (Jan 1987), pp. 21-25.

Eliabeth Carbide Die CO., Inc. "The Elizabeth Companies Tablet Design Training Manual," p. 7, McKeesport, PA.

Fegely, Kurt A., et al. The Effect of Tablet Shape on the Perception of High Gloss Film Coating System, Opaglos 2, High Gloss Film Coating System, COLORCON, Mar. 18, 2002.

Gunsel, Willian., C. et al. "Compression-Coated and Layer Tablets", Pharmaceutical Dosage Forms-Tablets, 1989, pp. 247-284. 2nd Edtion, vol. 1, Marcel Dekker, Inc. New York.

Hansson, Arne G., et al., "Perforated Coated Tablets for Controlled Release of Durgs at a Constant Rate", Journal of Pharmaceutical Sciences, Apr. 1988, vol. 77, No. 4, pp. 322-324.

Higuchi, T., "Mechanism of Sustained-Action Medication- Theoretical Analysis of Rate of Release of Solid Drugs Dispersed in Solid Matriced". Journal of Pharmaceutical Sciences, Dec. 1963, vol. 52, No. 12, pp. 1145-1149.

Higuchi, Takeru, "Rate of Release of Medicaments from Ointment Bases Containing Drugs in Suspension". Journal of Pharmaceutical Sciences, Oct. 1961, vol. 50, pp. 874-875.

Hsieh, Dean S.T. et al., "Zero-Order Controlled-Release Polymer Matricas for Micro and Macromolecules". Journal of Pharmaceutical Sciences, Jan. 1983, vol. 72, No. 1, pp. 1722.

Itoh. International Journal of Pharmaceutics 238 (2002) 153-160.

Kim, Chemg-ju, "Compressed Donut-Shaped Tablets with Zero-Order Release Kinetics", Pharmaceutical Research, Jul. 1994, vol. 12, No. 7, pp. 1045-1048.

Lipper, R.A. et al., "Analysis of Theoretical Behavior of a Proposed Zero-Order Drug Delivery System". Journal of Pharmaceutical Sciences, Feb. 1977, vol. 66, No. 2, pp. 163-164.

Lai, Jin-Wang. "Drug Release from Inert Matrices of Modified Geometry". The University of Iowa, University Microfilms International, 1985, pp. 29-59.

Leiberman et al. Pharmaceutical Dosage Forms-Tablets, vol. 2, 2nd ed., Marcel Dekker Inc., 1990, pp. 213-217, 247-284, 327-329.

Maffione, G., et al., "High-Viscosity HPMC as a Film-Coating Agent", Drug Development and Industrial Pharmacy, 1993, pp. 2043-2053, vol. 19, No. 16, Marcel Dekker, Inc. New York.

Minifie, Bernard C., Chocolate, Cocoa and Confectionary: Science and Technology, Jan. 1980, pp. 608-613, 2nd Edition, AVI Publishing Company, Inc., Westport, CT.

Nelson, K.G. et al., "Constant-Release Diffusion Systems- Rate Control by Means of Geometric Configuration". American Chemical Society, 1987, Chap. 24, pp. 325-340.

Porter, Stuart C., PhD., "Tablet Coating-Part 1", Drug Cosmet, Ind., May 1981, pp. 46-53 and 86-93, vol. 128.

Remington The Science and Practice of Pharmacy, pp. 208-209 (2000).

Rosato, Dominick V. et al., Injection Molding Handbook, 1986, Van Nostrand Reinhold Company.

Sangalli, M.E. et al., "Inert Monolithic Device with Central Hole for Constant Drug Release". Proceed Intern: Symp. Control. Rel Biosct. Meter. 20(1993), Controlled Release Society, Inc. pp. 316-317.

Samuelov, Y., et al., "Sustained Release of Drugs from Ethylcellulose-Polyethyiene Glycol Films and Kinetics of Drug Release". Journal of Pharmaceutical Sciences, Mar. 1979. vol. 68, No. 3, pp. 325-329.

Schneider, H., et al., "Contribution to Sugar Coating Tablets". Pharmaceutica Acta Helvetiae, pp. 394-410, vol. 43.

USP 24, 2000 Version, 19-20 and 856 (1999).

vehicle. Http://www2.merriam-webster.com/cgi-bin/mwmednim. Accessed Apr. 18, 2009.

* cited by examiner

METHOD OF MANUFACTURING MODIFIED RELEASE DOSAGE FORMS

This is a continuation of prior U.S. application Ser. No. 10/477,334 filed May 24, 2005, which is a national stage entry of PCT/US02/31022, filed Sep. 28, 2002, which is a continuation-in-part of U.S. application Ser. No. 09/966,939, filed Sep. 28, 2001 now U.S. Pat. No. 6,837,696, which is a continuation-in-part of U.S. application Ser. No. 09/966,450 filed on Sep. 28, 2001 now U.S. Pat. No. 6,982,094, which is a continuation-in-part of U.S. application Ser. No. 09/966,509 filed on Sep. 28, 2001 now U.S. Pat. No. 6,767,200, which is a continuation-in-part of U.S. application Ser. No. 09/966,497 filed on Sep. 28, 2001 now U.S. Pat. No. 7,122,143, which is a continuation-in-part of U.S. application Ser. No. 09/966,414 filed on Sep. 28, 2001 now abandoned, which are all incorporated by reference in their entireties herein.

BACKGROUND OF THE INVENTION

1. Field of the Invention

This invention relates to modified release dosage forms such as modified release pharmaceutical compositions. More particularly, this invention relates to modified release dosage forms in which a molded matrix provides for modified release of at least one active ingredient contained within the dosage form upon contacting of the dosage form with a liquid medium.

2. Background Information

Modified release pharmaceutical dosage forms have long been used to optimize drug delivery and enhance patient compliance, especially by reducing the number of doses of medicine the patient must take in a day. For this purpose, it is often desirable to modify the rate of release of a drug (one particularly preferred type of active ingredient) from a dosage form into the gastro-intestinal (g.i.) fluids of a patient, especially to slow the release to provide prolonged action of the drug in the body.

The rate at which an orally delivered pharmaceutical active ingredient reaches its site of action in the body depends on a number of factors, including the rate and extent of drug absorption through the g.i. mucosa. To be absorbed into the circulatory system (blood), the drug must first be dissolved in the g.i. fluids. For many drugs, diffusion across the g.i. membranes is relatively rapid compared to dissolution. In these cases, the dissolution of the active ingredient is the rate limiting step in drug absorption, and controlling the rate of dissolution allows the formulator to control the rate of drug absorption into the circulatory system of a patient.

An important objective of modified release dosage forms is to provide a desired blood concentration versus time (pharmacokinetic, or PK) profile for the drug. Fundamentally, the PK profile for a drug is governed by the rate of absorption of the drug into the blood, and the rate of elimination of the drug from the blood. The type of PK profile desired depends, among other factors, on the particular active ingredient, and physiological condition being treated.

One particularly desirable PK profile for a number of drugs and conditions, is one in which the level of drug in the blood is maintained essentially constant (i.e. the rate of drug absorption is approximately equal to the rate of drug elimination) over a relatively long period of time. Such systems have the benefit of reducing the frequency of dosing, improving patient compliance, as well as minimizing side effects while maintaining full therapeutic efficacy. A dosage form which provides a "zero-order," or constant, release rate of the drug is useful for this purpose. Since zero-order release systems are difficult to achieve, systems which approximate a constant release rate, such as for example first-order and square root of time profiles are often used to provide sustained (prolonged, extended, or retarded) release of a drug.

Another particularly desirable PK profile is achieved by a dosage form that delivers a delayed release dissolution profile, in which the release of drug from the dosage form is delayed for a pre-determined time after ingestion by the patient. The delay period ("lag time") can be followed either by prompt release of the active ingredient ("delayed burst"), or by sustained (prolonged, extended, or retarded) release of the active ingredient ("delayed then sustained").

Well known mechanisms by which a dosage form (or drug delivery system) can deliver drug at a controlled rate (e.g. sustained, prolonged, extended or retarded release) include diffusion, erosion, and osmosis.

One classic diffusion-controlled release system comprises a "reservoir" containing the active ingredient, surrounded by a "membrane" through which the active ingredient must diffuse in order to be absorbed into the bloodstream of the patient. The rate of drug release, (dM/dt) depends on the area (A) of the membrane, the diffusional pathlength (l), the concentration gradient ($\Delta C$) of the drug across the membrane, the partition coefficient (K) of the drug into the membrane, and the diffusion coefficient (D):

$$dM/dt = \{ADK\Delta C\}/l$$

Since one or more of the above terms, particularly the diffusional pathlength and concentration gradient tend to be non-constant, diffusion-controlled systems generally deliver a non-constant release rate. In general, the rate of drug release from diffusion-controlled release systems typically follows first order kinetics. One disadvantage of membrane-reservoir type systems is their vulnerability to "dose dumping." The diffusional membrane must remain intact without breach throughout the functional life of the dosage form in order to prevent this occurrence and the possibility of overdose along with the associated toxic side effects. One typical type of diffusional membrane-reservoir systems comprises a compressed tablet core which acts as the reservoir, surrounded by a shell (or coating) which functions as the diffusional membrane. Current core-shell systems are limited by the available methods for manufacturing them, as well as the materials that are suitable for use with the current methods. A shell, or coating, which confers modified release properties is typically applied via conventional methods, such as for example, spray-coating in a coating pan. Pan-coating produces a single shell which essentially surrounds the core. Defects that commonly occur during coating, include "picking," "sticking," and "twinning," all of which result in undesired holes in the coating, which lead to dose dumping. The coating compositions that can be applied via spraying are limited by their viscosity. High viscosity solutions are difficult or impractical to pump and deliver through a spray nozzle. Spray coating methods suffer the further limitations of being time-intensive and costly. Several hours of spraying may be required to spray an effective amount of coating to control the release of an active ingredient. Coating times of 8 to 24 hours are not uncommon.

Another common type of diffusion-controlled release system comprises active ingredient, distributed throughout an insoluble porous matrix through which the active ingredient must diffuse in order to be absorbed into the bloodstream of the patient. The amount of drug (M) released at a given time at sink conditions (i.e. drug concentration at the matrix surface is much greater than drug concentration in the bulk solution), depends on the area (A) of the matrix, the diffusion coefficient (D), the porosity (E) and tortuosity (T) of the matrix, the drug solubility (Cs) in the dissolution medium, time (t) and the drug concentration (Cp) in the dosage form:

$$M=A(DE/T(2Cp-ECs)(Cs)t)^{1/2}$$

It will be noted in the above relationship that the amount of drug released is generally proportional to the square root of time. Assuming factors such as matrix porosity and tortuosity are constant within the dosage form, a plot of amount of drug released versus the square root of time should be linear. One typical type of diffusional matrix system may be prepared by compression of the active ingredient along with a mixture of soluble and insoluble materials designed to produce a desired porosity and tortuosity as the soluble materials dissolve in the dissolution medium or gastro-intestinal fluids.

A commonly used erosion-controlled release system comprises a "matrix" throughout which the drug is distributed. The matrix typically comprises a material which swells at the surface, and slowly dissolves away layer by layer, liberating drug as it dissolves. The rate of drug release, (dM/dt), in these systems depends on the rate of erosion (dx/dt) of the matrix, the concentration profile in the matrix, and the surface area (A) of the system:

$$dM/dt=A\{dx/dt\}\{f(C)\}$$

Again, variation in one or more terms, such as surface area, typically leads to a non-constant release rate of drug. In general, the rate of drug release from erosion-controlled release systems typically follows first order kinetics. One typical method of preparing such eroding matrix systems is by compression of the active ingredient blended with a mixture of compressible excipients comprising water swellable erodible materials which create a temporary barrier as they swell, and allow small amounts of active ingredient to be released as the continuously receding surface layer slowly dissolves in the dissolution medium or gastro-intestinal fluids.

Another type of erosion controlled delivery system employs materials which swell and dissolve slowly by surface erosion to provide a delayed release of pharmaceutical active ingredient. Delayed release is useful, for example in pulsatile or repeat action delivery systems, in which an immediate release dose is delivered, followed by a pre-determined lag time before a subsequent dose is delivered from the system. In these systems, the lag time ($T_1$) depends on the thickness (h) of the erodible layer, and the rate of erosion (dx/dt) of the matrix, which in turn depends on the swelling rate and solubility of the matrix components:

$$T_1=h(dx/dt)$$

The cumulative amount of drug (M) released from these systems at a given time generally follows the equation:

$$M=(dM/dt)(t-T_1)$$

where dM/dt is generally described by either the diffusion-controlled or erosion-controlled equations above, and $T_1$ is the lag time.

Modified release dosage forms prepared via compression to obtain either diffusional or eroding matrices are exemplified in U.S. Pat. Nos. 5,738,874 and 6,294,200, and WO 99/51209. Compressed dosage forms are limited by the achievable geometry's, as well as the suitable materials for producing them.

WO 97/49384 describes a hot-melt extrudable mixture of a therapeutic compound and a high molecular weight poly(ethylene oxide). In some embodiments, the formulation further comprises poly(ethylene glycol). The high molecular weight poly(ethylene oxide)s employed have molecular weights ranging from about 1 to about 10 million Daltons. The minimum ratio of high molecular weight poly(ethylene oxide) to active ingredient is 80:20. The dosage forms of this reference are limited in the amount of active ingredient they can deliver. The maximum amount of active ingredient that may be delivered in the composition is not more that 20 weight percent of the composition. Typical hot-melt systems are additionally limited by high processing temperatures, and are therefore not optimal for delivering low melting, or heat labile active ingredients. Typical hot-melt systems are additionally not optimal for delivering coated particles of active ingredients, due to both the high processing temperatures, and the high shear imparted during processing through extruders or spray nozzles.

It would be desirable to have a versatile and cost-effective method for preparing modified release matrix systems, which are not susceptible to dose dumping. It would additionally be desirable to have a method for preparing modified release matrix systems in a variety of shapes, for either functional purposes, e.g. achieving a desired release profile using certain advantageous geometries, or for consumer preference purposes, such as swallowability, dosage form elegance, and product identification and differentiation. It would additionally be desirable to have modified release matrix systems comprising a matrix which is transparent, semi-transparent, or translucent, through which various types of particles are visible to the consumer. It would additionally be desirable to have a controlled release matrix systems capable of delivering a relatively high level of active ingredient in a relatively small dosage form. It would additionally be desirable to have modified release matrix systems for delivering low-melting or heat labile active ingredients. It would additionally be desirable to have modified release matrix systems capable of delivering coated particles of active ingredient.

It is one object of this invention to provide a dosage form in which at least one active ingredient contained therein exhibits a modified release profile upon contacting of the dosage form with a liquid medium. Other objects, features and advantages of the invention will be apparent to those skilled in the art from the detailed description set forth below.

SUMMARY OF THE INVENTION

In one embodiment the dosage form of this invention of this invention comprises a molded matrix and at least one active ingredient. The matrix comprises 10-100% of a material having a melting point of less than about 100° C., selected from the group consisting of thermoplastic polyalkalene oxides, low melting hydrophobic materials, thermoplastic polymers, thermoplastic starches and combinations thereof and the matrix is capable of providing modified release of the active ingredient upon contacting of the dosage form with a liquid medium.

In another embodiment the dosage form comprises a molded matrix and at least one active ingredient at a level of more than about 20 weight percent. The matrix comprises 10-100% of a material having a melting point of less than about 100 degrees C., and the matrix is capable of providing modified release of the active ingredient upon contacting of the dosage form with a liquid medium.

In another embodiment, the dosage form comprises a plurality of particles, and at least a portion of the particles comprise at least one active ingredient.

In another embodiment, at least a portion of the particles are coated with a coating capable of providing modified release of the active ingredient contained therein upon contacting of the dosage form with a liquid medium.

In another embodiment, at least a portion of the particles are coated with a coating comprising means for providing modified release of the active ingredient contained therein upon contacting of the dosage form with a liquid medium.

In another embodiment, at least a portion of the particles are coated with a coating comprising 10-100 wt. % of a release-modifying polymer selected from the group consisting of pH-dependent polymers, water-soluble polymers, water-insoluble polymers, and copolymers, derivatives and mixtures thereof.

In another embodiment, the matrix comprises at least one active ingredient.

In another embodiment, upon contacting of the dosage form with a liquid medium, at least a portion of the active ingredient is released in a sustained manner.

In another embodiment, the dosage form releases active ingredient at a substantially constant rate.

In another embodiment, upon contacting of the dosage form with a liquid medium, a time delay occurs prior to release of at least a portion of the active ingredient.

In another embodiment, the portion of the active ingredient released after the time delay is released in a sustained manner.

In another embodiment, the dosage form additionally comprises a plurality of particles and a matrix which comprises a first dose of active ingredient. At least a portion of the particles comprise a second dose of active ingredient which may be the same or different than the first active ingredient, and upon contacting of the dosage form with a liquid medium, immediate release of the first dose of active ingredient occurs followed by a lag time, followed by delayed release of the second dose of active ingredient.

In another embodiment, the dosage form additionally comprises a plurality of particles and a matrix which comprises a first dose of active ingredient. At least a portion of the particles comprise a second dose of active ingredient which is the same or different than the first active ingredient, and upon contacting of the dosage form with a liquid medium, immediate release of the first dose of active ingredient occurs followed by sustained release of the second dose of active ingredient.

In another embodiment, the dosage form comprises at least one active ingredient, a molded matrix and a plurality of particles dispersed in the matrix, wherein at least a portion of the particles are coated, and the dosage form is capable of providing modified release of the active ingredient upon contacting of the dosage form with a liquid medium.

In another embodiment, the matrix is capable of providing modified release of the active ingredient upon contacting of the dosage form with a liquid medium.

In another embodiment, the dosage form further comprises at least one uncoated active ingredient dispersed in the matrix.

In another embodiment, at least a portion of the coated particles comprise at least one active ingredient and are coated with a coating capable of providing modified release of the active ingredient contained therein upon contacting of the coated particle with a liquid medium.

In another embodiment, at least a portion of the particles are coated with a coating comprising 10-100 wt. % of a release-modifying polymer selected from the group consisting of pH-dependent polymers, water-soluble polymers, water-insoluble polymers, and copolymers, derivatives and mixtures thereof.

In another embodiment, upon contacting of the dosage form with a liquid medium, at least a portion of the active ingredient is released in a sustained manner.

In another embodiment, the dosage form releases at least a portion of the active ingredient at a substantially constant rate.

In another embodiment, upon contacting of the dosage form with a liquid medium, a time delay occurs prior to release of at least a portion of the active ingredient.

In another embodiment, the portion of the active ingredient released after the time delay is released in a sustained manner.

In another embodiment, the dosage form comprises first and second doses of active ingredients which may be the same or different, and upon contacting of the dosage form with a liquid medium, the first dose of active ingredient is released in a sustained manner, and a time delay precedes release of the second active ingredient.

In another embodiment, the matrix contains a first active ingredient dispersed therein and at least a portion of the particles comprise a second active ingredient which may be the same or different than the first active ingredient, and upon contacting of the dosage form with a liquid medium, immediate release of the first active ingredient occurs followed by a time delay, followed by release of the second active ingredient.

In another embodiment, the matrix contains a first active ingredient dispersed therein and at least a portion of the particles comprise a second active ingredient which is the same or different than the first active ingredient, and upon contacting of the dosage form with a liquid medium, immediate release of the first active ingredient occurs followed by sustained release of the second active ingredient.

In another embodiment, the thermal reversible carrier is selected from the group consisting of polycaprolactones, polyvinyl acetate, polyalkylene glycols and combinations thereof.

In another embodiment, in which the thermal reversible carrier is selected from the group consisting of polyethylene glycol having molecular weight from about 100 to about 20,000 Daltons, polyethylene oxide having a molecular weight from about 100,000 to about 900,000 Daltons, and combinations thereof.

In another embodiment, the thermal reversible carrier is from about 30 to about 70 weight percent of the matrix.

In another embodiment, the molded matrix further comprises a release-modifying moldable excipient selected from the group consisting of swellable erodible hydrophilic materials, pH-dependent polymers, insoluble edible materials, and pore-formers and combinations thereof.

In another embodiment, the level of release-modifying excipient is from about 1 percent to about 55 percent by weight of the molded matrix.

In another embodiment, the release-modifying excipient is shellac.

In another embodiment, the molded matrix further comprises a release-modifying excipient, and the release-modifying excipient is croscarmellose sodium.

In another embodiment, the dosage form further comprises tributyl citrate as a plasticizer.

DETAILED DESCRIPTION OF THE INVENTION

As used herein, the term "dosage form" applies to any solid object, semi-solid, or liquid composition designed to contain a specific pre-determined amount (i.e. dose) of a certain ingredient, for example an active ingredient as defined below. Suitable dosage forms may be pharmaceutical drug delivery systems, including those for oral administration, buccal administration, rectal administration, topical or mucosal delivery, or subcutaneous implants, or other implanted drug delivery systems; or compositions for delivering minerals, vitamins and other nutraceuticals, oral care agents, flavorants, and the like. Preferably the dosage forms of the present invention are considered to be solid, however they may contain liquid or semi-solid components. In a particularly preferred embodiment, the dosage form is an orally administered system for delivering a pharmaceutical active ingredient to the gastro-intestinal tract of a human.

The dosage forms of the invention exhibit modified release of one or more active ingredients contained therein. One or more active ingredients may be found within the molded matrix, or coated or uncoated particles distributed therethrough. As used herein, the term "modified release" shall apply to dosage forms, matrices, particles, coatings, portions thereof, or compositions that alter the release of an active ingredient in any manner. Types of modified release include controlled, prolonged, sustained, extended, delayed, pulsatile, repeat action, and the like. Suitable mechanisms for achieving these types of modified release include diffusion, erosion, surface area control via geometry and/or impermeable barriers, or other mechanisms known in the art. Moreover, the modified release properties of the dosage form may be achieved through design of the matrix or a portion thereof, or a combination of matrix design with other features of the dosage form.

Figure 1A:
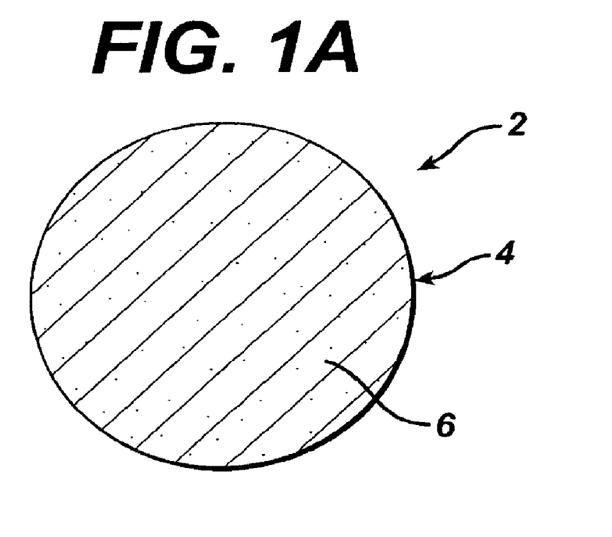
FIG. 1A depicts a cross-sectional side view of one embodiment of the dosage form of this invention.

A first embodiment of this invention is depicted in FIG. 1A, which is a cross-sectional side view of a dosage form 2 which comprises a molded matrix 4 and a plurality of uncoated particles 6 which are contained within the matrix 4. In this embodiment, the matrix comprises 10-100% by weight of the matrix of a material having a melting point of less than about 100° C. The active ingredient or ingredients may be contained in the matrix, the particles, or a combination thereof. The matrix provides modified release of the active ingredient upon contacting of the dosage form with a liquid medium such as water, gastrointestinal fluid and the like. In other embodiments, the molded matrix 4 may contain active ingredient which is not in the form of particles.

Figure 1B:
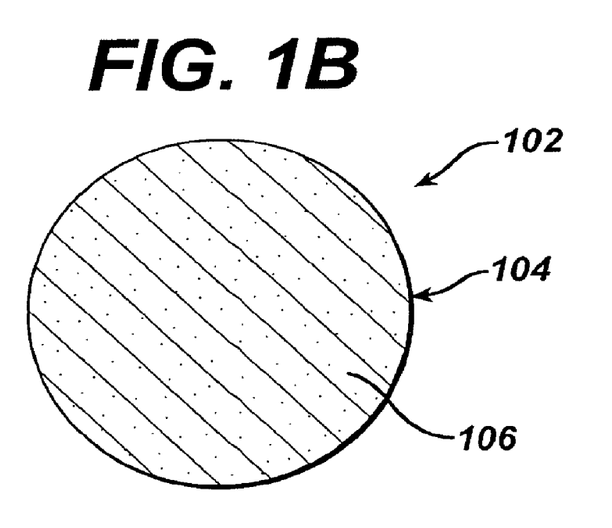
FIG. 1B depicts a cross-sectional side view of another embodiment of the dosage form of this invention.

Another embodiment of this invention is depicted in FIG. 1B, which is a cross-sectional side view of a dosage form 102 which comprises a molded matrix 104 containing a plurality of particles and at least a portion of the particles contained within the matrix are coated particles 106. In this particular embodiment, it is not required that the matrix comprise a material have a melting point of less than 100° C. The active ingredient or ingredients may be contained in the matrix, the coated particles, or a combination thereof. Either the particle coating, the matrix or both may provide modified release of the active ingredient upon contacting of the dosage form with a liquid medium such as water, gastrointestinal fluid and the like.

The active ingredient or ingredients employed in the dosage forms of this invention may be found within the matrix, the particles (whether coated or uncoated) or a combination thereof. Suitable active ingredients for use in this invention include for example pharmaceuticals, minerals, vitamins and other nutraceuticals, oral care agents, flavorants and mixtures thereof. Suitable pharmaceuticals include analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, diuretics, expectorants, gastrointestinal agents, migraine preparations, motion sickness products, mucolytics, muscle relaxants, oral contraceptives, osteoporosis preparations, polydimethylsiloxanes, respiratory agents, sleep-aids, urinary tract agents and mixtures thereof.

Suitable oral care agents include breath fresheners, tooth whiteners, antimicrobial agents, tooth mineralizers, tooth decay inhibitors, topical anesthetics, mucoprotectants, and the like.

Suitable flavorants include menthol, peppermint, mint flavors, fruit flavors, chocolate, vanilla, bubble gum flavors, coffee flavors, liqueur flavors and combinations and the like.

Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotadine, ranitidine, cimetadine, nizatidine; proton pump inhibitors such as omeprazole or lansoprazole; gastrointestinal cytoprotectives, such as sucraflate and misoprostol; gastrointestinal prokinetics, such as prucalopride, antibiotics for *H. pylori*, such as clarithromycin, amoxicillin, tetracycline, and metronidazole; antidiarrheals, such as diphenoxylate and loperamide; glycopyrrolate; antiemetics, such as ondansetron, analgesics, such as mesalamine.

In one embodiment of the invention, the active ingredient or agent may be selected from bisacodyl, famotadine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, the active ingredient is selected from analgesics, anti-inflammatories, and antipyretics, e.g. non-steroidal anti-inflammatory drugs (NSAIDs), including propionic acid derivatives, e.g. ibuprofen, naproxen, ketoprofen and the like; acetic acid derivatives, e.g. indomethacin, diclofenac, sulindac, tolmetin, and the like; fenamic acid derivatives, e.g. mefanamic acid, meclofenamic acid, flufenamic acid, and the like; biphenylcarbodylic acid derivatives, e.g. diflunisal, flufenisal, and the like; and oxicams, e.g. piroxicam, sudoxicam, isoxicam, meloxicam, and the like. In a particularly preferred embodiment, the active ingredient is selected from propionic acid derivative NSAID, e.g. ibuprofen, naproxen, flurbiprofen, fenbufen, fenoprofen, indoprofen, ketoprofen, fluprofen, pirprofen, carprofen, oxaprozin, pranoprofen, suprofen, and pharmaceutically acceptable salts, derivatives, and combinations thereof. In a particular embodiment of the invention, the active ingredient may be selected from acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

In another embodiment of the invention, the active ingredient may be selected from pseudoephedrine, phenylpropanolamine, chlorpheniramine, dextromethorphan, diphenhydramine, astemizole, terfenadine, fexofenadine, loratadine, desloratadine, cetirizine, mixtures thereof and pharmaceutically acceptable salts, esters, isomers, and mixtures thereof.

Examples of suitable polydimethylsiloxanes, which include, but are not limited to dimethicone and simethicone, are those disclosed in U.S. Pat. Nos. 4,906,478, 5,275,822, and 6,103,260. As used herein, the term "simethicone" refers to the broader class of polydimethylsiloxanes, including but not limited to simethicone and dimethicone.

The active ingredient or ingredients are present in the dosage form in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dose regime, the age and weight of the patient, and other factors must be considered, as known in the art. In a preferred embodiment the dosage form comprises one or more active ingredient or ingredients at a combined level of more than about 20 weight percent, e.g. at least about 25 weight percent, or at least about 30 weight percent, or at least about 50 weight percent of the dosage form.

The active ingredient or ingredients may be present in the dosage form in any form. For example, the active ingredient may be dispersed at the molecular level, e.g. melted or dissolved, within the dosage form, or may be in the form of particles, which in turn may be coated or uncoated. If the active ingredient is in form of particles, the particles (whether coated or uncoated) typically have an average particle size of about 1-2000 microns. In one preferred embodiment, such particles are crystals having an average particle size of about 1-300 microns. In another preferred embodiment, the particles are granules or pellets having an average particle size of about 50-2000 microns, preferably about 50-1000 microns, most preferably about 100-800 microns.

The molded matrix of the present invention is made by molding, preferably using a solvent-free process. In a preferred embodiment, the matrix comprises a flowable material. The flowable material may be any edible material that is flowable at a temperature between about 37° C. and about 250° C., and that is solid, semi-solid, or can form a gel at a temperature between about −10° C. and about 80° C. In a preferred embodiment, the flowable material comprises 10-100% by weight of a thermal reversible carrier having a melting point of less than about 100° C., preferably from about 20 to about 100° C.; and optionally up to about 30 weight percent of various adjuvants such as for example plasticizers, gelling agents, colorants, stabilizers, preservatives, and the like as known in the art. The matrix may optionally further comprise up to about 55 weight percent of one or more release-modifying excipients as described below.

In embodiments of this invention in which the matrix comprises 10-100% by weight of a thermal reversible carrier having a melting point of less than about 100° C., such low melting materials may include, for example thermoplastic polyalkalene oxides, low melting hydrophobic materials, thermoplastic polymers, thermoplastic starches, and the like. Preferred low-melting materials may be selected from thermoplastic polymers, thermoplastic polyalkalene oxides, low melting hydrophobic materials, and combinations thereof.

Suitable thermal-reversible carriers for making the molded matrix include are thermoplastic materials typically having a melting point below about 110° C., more preferably between about 20 and about 100° C. Examples of suitable thermal-reversible carriers for solvent-free molding include thermoplastic polyalkalene glycols, thermoplastic polyalkalene oxides, low melting hydrophobic materials, thermoplastic polymers, thermoplastic starches, and the like. Preferred thermal-reversible carriers include polyethylene glycol and poly-ethylene oxide. Suitable thermoplastic polyalkylene glycols for use as thermal-reversible carriers include polyethylene glycol having molecular weight from about 100 to about 20,000, e.g. from about 100 to about 8,000, say about 1000 to about 8,000 Daltons. Suitable thermoplastic polyalkalene oxides include polyethylene oxide having a molecular weight from about 100,000 to about 900,000 Daltons. Suitable low-melting hydrophobic materials for use as thermal-reversible carriers include fats, fatty acid esters, phospholipids, and waxes which are solid at room temperature, fat-containing mixtures such as chocolate; and the like. Examples of suitable fats include hydrogenated vegetable oils such as for example cocoa butter, hydrogenated palm kernel oil, hydrogenated cottonseed oil, hydrogenated sunflower oil, and hydrogenated soybean oil; and free fatty acids and their salts. Examples of suitable fatty acid esters include sucrose fatty acid esters, mono, di, and triglycerides, glyceryl behenate, glyceryl palmitostearate, glyceryl monostearate, glyceryl tristearate, glyceryl trilaurylate, glyceryl myristate, Glyco-Wax-932, lauroyl macrogol-32 glycerides, and stearoyl macrogol-32 glycerides. Examples of suitable phospholipids include phosphotidyl choline, phosphotidyl serene, phosphotidyl enositol, and phosphotidic acid. Examples of suitable waxes which are solid at room temperature include carnauba wax, spermaceti wax, beeswax, candelilla wax, shellac wax, microcrystalline wax, and paraffin wax.

In one preferred embodiment, the matrix comprises a low-melting thermal-reversible carrier selected from polycaprolactones, polyvinyl acetate, polyalkylene glycols and combinations thereof at a level of about 30 to about 70 weight percent, e.g. about 35 to about 50 weight percent of the matrix. The low-melting thermal-reversible polymer has a melting point of less than about 100° C. In one such embodiment, the matrix further comprises a thermoplastic polyethylene oxide at a level of about 15 to about 25% as a strengthening polymer. Polyethylene oxides having suitable thermoplastic properties for use in the present invention have a molecular weight of about 100,000 to about 900,000. In another such embodiment, the matrix is substantially free of poly(ethylene oxide), e.g. contains less than 1%, or contains less than 0.1 weight percent of poly(ethylene oxide).

In other embodiments of this invention in which it is not required that the matrix comprise a thermal reversible carrier have a melting point of less than 100° C., the matrix composition may comprise any of the materials set forth above having a melting point of less than 100° C., and the matrix composition may also comprise other materials such as release modifying agents, various adjuvants such as for example plasticizers, gelling agents, colorants, stabilizers, preservatives, and the like as known in the art.

Suitable release-modifying moldable excipients for making the molded matrix, or a portion thereof, by molding include but are not limited to swellable erodible hydrophilic materials, pH-dependent polymers, insoluble edible materials, and pore-formers.

Suitable swellable erodible hydrophilic materials for use as release-modifying excipients for making the molded matrix, or a portion thereof, by molding include water soluble cellulose derivatives such as for example sodium carboxymethylcellulose, cross-linked hydroxypropylcellulose, hydroxypropyl cellulose, hydroxypropylmethylcellulose, hydroxyisopropylcellulose, hydroxybutylcellulose, hydroxyphenylcellulose, hydroxyethylcellulose, hydroxypentylcellulose, hydroxypropylethylcellulose, hydroxypropylbutylcellulose, hydroxypropylethylcellulose polyethylene glycols, poly(ethylene oxide), potassium methacrylate divinylbenzene copolymer, polymethylmethacrylate, CAR- BOPOL (high-molceular weight crosslinked acrylic acid homopolymers and copolymers), and the like; hydrocolloids such as for example alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan, clays, gelling starches such as acid hydrolyzed starches and derivatives and mixtures there of; cross-linked polyvinyl pyrrolidone, cross-linked agar, sodium starch glycolate, and croscarmellose sodium.

Suitable pH-dependent polymers for use as release-modifying excipients for making the molded matrix or a portion thereof by molding include enteric cellulose derivatives such as for example hydroxypropyl methylcellulose phthalate, hydroxypropyl methylcellulose acetate succinate, cellulose acetate phthalate, shellac, enteric acetate derivatives such as for example polyvinylacetate phthalate, and enteric acrylate derivatives such as for example polymethacrylate-based polymers such as poly(methacrylic acid, methyl methacrylate) 1:2, which is commercially available from Rohm Pharma GmbH under the tradename EUDRAGIT S polymers, and poly(methacrylic acid, methyl methacrylate) 1:1, which is commercially available from Rohm Pharma GmbH under the tradename EUDRAGIT L polymers.

Suitable insoluble edible materials for use as release-modifying excipients for making the molded matrix, or a portion thereof, my molding include water-insoluble polymers such as for example acrylates, acrylic acid copolymers, cellulose acetate, cellulose acetate propionate, cellulose acetate propionate, cellulose propionate, cellulose acetate butyrate, cellulose acetate phthalate, acetaldehyde dimethylcellulose acetate, cellulose acetate ethyl carbamate, cellulose acetate methyl carbamate, cellulose acetate diethyl aminoacetate, ethylcellulose, methacrylates, polyvinyl alcohols, polyvinyl acetate, polycaprolactones, and the like; fats such as for example cocoa butter, hydrogenated vegetable oils such as palm kernel, cottonseed oil, sunflower oil, and soybean oil, mono, di, and triglycerides, phospholipids, long-chain fatty acids, fatty acid esters; and waxes such as for example carnauba wax, spermaceti wax, beeswax, candelilla wax, shellac wax, microcrystalline wax, and paraffin wax.

Suitable pore-formers for use as release-modifying excipients for making the molded matrix or a portion thereof by molding include water-soluble organic and inorganic materials. Examples of suitable water-soluble organic materials include water soluble polymers including water soluble cellulose derivatives such as hydroxypropylmethylcellulose, hydroxypropylcellulose, water soluble carbohydrates such as sugars, starches; water soluble polymers such as polyvinylpyrrolidone, polyethylene glycol; microcrystalline cellulose; salts such as sodium chloride and potassium chloride and the like and/or mixtures thereof.

Suitable plasticizers for making the molded matrix, or a portion thereof, by molding, include triacetin, acetylated monoglyceride, rape oil, olive oil, sesame oil, acetyltributyl citrate, glycerin sorbitol, diethyloxalate, diethylmalate, diethyl fumarate, dibutyl succinate, diethylmalonate, dioctylphthalate, dibutylsuccinate, triethylcitrate, tributylcitrate, glyceroltributyrate, propylene glycol, polyethylene glycols, hydrogenated castor oil, fatty acids, substituted triglycerides and glycerides, and the like.

The matrix may be in a variety of different shapes. For example, the matrix may be shaped as a polyhedron, such as a cube, pyramid, prism, or the like; or may have the geometry of a space figure with some non-flat faces, such as a cone, truncated cone, cylinder, sphere, torus, or the like. In certain embodiments, the matrix has one or more major faces. For example in certain embodiments matrix surface may have two opposing major faces formed by contact with upper and lower mold surfaces. In such embodiments the matrix surface may further comprise a "belly-band" located between the two major faces, and formed by contact with the side walls in the mold.

In one embodiment of the invention, the matrix is made by the thermal setting molding method and apparatus described in copending U.S. patent application Ser. No. 09/966,450, pages 57-63, the disclosure of which is incorporated herein by reference. In this embodiment, the matrix is formed by injecting a starting material in flowable form into a molding chamber. The starting material preferably comprises an active ingredient and a thermal setting material at a temperature above the melting point of the thermal setting material but below the decomposition temperature of the active ingredient. The starting material is cooled and solidifies in the molding chamber into a shaped form (i.e., having the shape of the mold).

According to this method, the starting material must be in flowable form. For example, it may comprise solid particles suspended in a molten matrix, for example a polymer matrix. The starting material may be completely molten or in the form of a paste. The starting material may comprise an active ingredient dissolved in a molten material. Alternatively, the starting material may be made by dissolving a solid in a solvent, which solvent is then evaporated from the starting material after it has been molded.

The starting material may comprise any edible material which is desirable to incorporate into a shaped form, including active ingredients, nutritionals, vitamins, minerals, flavors, sweeteners, and the like. Preferably, the starting material comprises an active ingredient and a thermal setting material. The thermal setting material may be any edible material that is flowable at a temperature between about 37 and about 120° C., and that is a solid at a temperature between about 0 and about 35° C. Preferred thermal setting materials include water-soluble polymers such as polyalkylene glycols, polyethylene oxides and derivatives, and sucrose esters; fats such as cocoa butter, hydrogenated vegetable oil such as palm kernel oil, cottonseed oil, sunflower oil, and soybean oil; mono-, di-, and triglycerides, phospholipids, waxes such as carnuba wax, spermaceti wax, beeswax, candelilla wax, shellac wax, microcrystalline wax, and paraffin wax; fat-containing mixtures such as chocolate; sugar in the form on an amorphous glass such as that used to make hard candy forms, sugar in a supersaturated solution such as that used to make fondant forms; low-moisture polymer solutions such as mixtures of gelatin and other hydrocolloids at water contents up to about 30% such as those used to make "gummi" confection forms. In a particularly preferred embodiment, the thermal setting material is a water-soluble polymer such as polyethylene glycol.

In another embodiment of the invention, the matrix is make using the thermal cycle molding method and apparatus described in copending U.S. patent application Ser. No. 09/966,497, pages 27-51, the disclosure of which is also incorporated herein by reference. In the thermal cycle molding method and apparatus of U.S. patent application Ser. No. 09/966,497, a thermal cycle molding module having the general configuration shown in FIG. 3 therein is employed. The thermal cycle molding module 200 comprises a rotor 202 around which a plurality of mold units 204 are disposed. The thermal cycle molding module includes a reservoir 206 (see FIG. 4) for holding flowable material to make the matrix. In addition, the thermal cycle molding module is provided with a temperature control system for rapidly heating and cooling the mold units. FIGS. 55 and 56 depict such a temperature control system 600.

If particles are contained in the matrix, the particles (whether coated or uncoated) Typically have an average particle size of about 1-2000 microns. In one preferred embodiment, the particles are crystals of the active ingredient or ingredients, and the average particle size is about 1-300 microns. In another preferred embodiment, the particles are granules or pellets, and the average particle size is about 50-2000 microns, preferably about 50-1000 microns, most preferably about 100-800 microns.

In particular embodiments of this invention in which uncoated particles are employed, the particles may comprise active ingredient as described herein, or may be inactive particles included for example to provide a visual distinction to the appearance of the dosage form.

In one particular embodiment, the matrix material may be transparent, semi-transparent, or translucent. In one such embodiment, the particles, either coated or uncoated, and either active or inactive, may be visible from the outside of the dosage form.

In particular embodiments of this invention in which coated particles are employed, the particles may be as described herein, and the particle coating may comprise about 10-100 weight percent (based on the weight of the coating) of a film former; optionally up to about 50 weight percent based on the weight of the coating of a pore former; and optionally up to about 30 weight percent of various adjuvants or excipients such as plasticizers etc. The particles may be coated using conventional coating technology which is well known to those skilled in the art including microencapsulation techniques such as coacervation, spray-drying, and fluidized bed coating including tangential spray rotor coating and bottom spray wurster coating. Examples of suitable particle coating methods and materials can be found in U.S. Pat. Nos. 5,286,497; 4,863,742; 4,173,626; 4,980,170; 4,984,240; 5,912,013; 6,270,805; and 6,322,819. Such coated particles may provide controlled release of the active ingredient contained therein in certain embodiments.

Suitable film formers for particle coating include, but are not limited to, film-forming water soluble polymers, film-forming proteins, film-forming water insoluble polymers, and film-forming pH-dependent polymers. In one embodiment, the film-former for particle coating may be selected from cellulose acetate, ammonio methacrylate copolymer type B, shellac, hydroxypropylmethylcellulose, and polyethylene oxide, and combinations thereof.

Suitable film-forming water soluble polymers for particle coating include water soluble vinyl polymers such as polyvinylalcohol; water soluble polycarbohydrates such as hydroxypropyl starch, hydroxyethyl starch, pullulan, methylethyl starch, carboxymethyl starch, pre-gelatinized starches, and film-forming modified starches; water swellable cellulose derivatives such as hydroxypropyl cellulose (HPC), hydroxypropylmethyl cellulose (HPMC), methyl cellulose (MC), hydroxyethylmethylcellulose (HEMC), hydroxybutylmethylcellulose (HBMC), hydroxyethylethylcellulose (HEEC), and hydroxyethylhydroxypropylmethyl cellulose (HEMPMC); water soluble copolymers such as methacrylic acid and methacrylate ester copolymers, polyvinyl alcohol and polyethylene glycol copolymers, polyethylene oxide and polyvinylpyrrolidone copolymers; and derivatives and combinations thereof.

Suitable film-forming proteins may be natural or chemically modified, and include gelatin, whey protein, myofibrillar proteins, coaggulatable proteins such as albumin, casein, caseinates and casein isolates, soy protein and soy protein isolates, zein; and polymers, derivatives and mixtures thereof.

In embodiments in which the particle coating confers modified release to one or more active ingredients contained in the particle, suitable film formers may be selected from film forming water insoluble polymers; film forming pH-dependent polymers; and copolymers and combinations thereof. In certain such embodiments in which the particle coating functions as a diffusional membrane, the release-modifying particle coating preferably comprises a pore former.

Suitable film forming water insoluble polymers for use in release-modifying particle coatings include for example ethylcellulose, polyvinyl alcohols, polyvinyl acetate, polycaprolactones, cellulose acetate and its derivatives, acrylates, methacrylates, acrylic acid copolymers; and the like and derivatives, copolymers, and combinations thereof.

Suitable film forming pH-dependent polymers for use in release-modifying particle coatings include for example enteric cellulose derivatives, such as for example hydroxypropyl methylcellulose phthalate, hydroxypropyl methylcellulose acetate succinate, cellulose acetate phthalate; natural resins, such as shellac and zein; enteric acetate derivatives such as for example polyvinylacetate phthalate, cellulose acetate phthalate, acetaldehyde dimethylcellulose acetate; and enteric acrylate derivatives such as for example polymethacrylate-based polymers such as poly(methacrylic acid, methyl methacrylate) 1:2, which is commercially available from Rohm Pharma GmbH under the tradename EUDRAGIT S, and poly(methacrylic acid, methyl methacrylate) 1:1, which is commercially available from Rohm Pharma GmbH under the tradename EUDRAGIT L; and the like, and derivatives, salts, copolymers, and combinations thereof.

Suitable pore formers for use in release-modifying particle coatings include water-soluble organic and inorganic materials. In one embodiment the pore former is selected from hydroxypropylcellulose and hydroxypropylmethylcellulose. Examples of suitable water-soluble organic materials include water soluble cellulose derivatives such as hydroxypropylmethylcellulose, and hydroxypropylcellulose; water soluble carbohydrates such as sugars, and starches; water soluble polymers such as polyvinylpyrrolidone and polyethylene glycol, and insoluble swelling polymers such as microcrystalline cellulose. Examples of suitable water soluble inorganic materials include salts such as sodium chloride and potassium chloride and the like and/or mixtures thereof.

Examples of suitable adjuvants or excipients for particle coatings include plasticizers, detackifiers, humectants, surfactants, anti-foaming agents, colorants, opacifiers, and the like. Suitable plasticizers include, but not be limited to polyethylene glycol; propylene glycol; glycerin; sorbitol; triethyl citrate; tribuyl citrate; dibutyl sebecate; vegetable oils such as castor oil, rape oil, olive oil, and sesame oil; surfactants such as polysorbates, sodium lauryl sulfates, and dioctyl-sodium sulfosuccinates; mono acetate of glycerol; diacetate of glycerol; triacetate of glycerol; natural gums; triacetin; acetyltributyl citrate; diethyloxalate; diethylmalate; diethyl fumarate; diethylmalonate; dioctylphthalate; dibutylsuccinate; glyceroltributyrate; hydrogenated castor oil; fatty acids; substituted triglycerides and glycerides; and the like and/or mixtures thereof. In one embodiment, the plasticizer is triethyl citrate. In certain embodiments, the shell is substantially free of plasticizers, i.e. contains less than about 1%, say less than about 0.01% of plasticizers.

In certain particularly preferred embodiments of this invention, the dosage form releases one or more active ingredients contained therein in a sustained, extended, prolonged, or retarded manner, more preferably at a substantially constant rate upon contacting of the dosage form with a liquid medium. In such embodiments, the molded matrix may function as a diffusional matrix or an eroding matrix. In embodiments in which the molded matrix functions as an eroding matrix from which dispersed active ingredient is liberated in a sustained, extended, prolonged, or retarded manner, the molded matrix preferably comprises a release-modifying moldable excipient selected from swellable erodible hydrophilic materials, pH-dependent polymers, insoluble edible materials, and combinations thereof. In embodiments in which the molded matrix functions as a diffusional matrix through which active ingredient contained therein is liberated in a sustained, extended, prolonged, or retarded manner, the molded matrix preferably comprises a release-modifying excipient selected from combinations of insoluble edible materials and pore formers. Alternately, in such embodiments in which the matrix is prepared by solvent-free molding, the thermal-reversible carrier may function by dissolving and forming pores or channels through which the active ingredient may be liberated.

In certain other preferred embodiments of this invention, the dosage form releases at least first and second active ingredients contained therein in a sustained, extended, prolonged, or retarded manner. In certain such embodiments, the first and second active ingredients have different unmodified release characteristics; however the dosage form advantageously provides different types of modification to the first and second active ingredients, such that the dissolution profiles of the first and second active ingredients from the dosage form are similar. In certain other such embodiments, the dosage form advantageously provides different types of modification to the first and second active ingredients, such that the dissolution profiles of the first and second active ingredients from the dosage form are substantially different, e.g. the first and second active ingredients are released from the dosage for at different rates or times upon contacting of the dosage form with a liquid medium. In a particularly preferred embodiment, the first and second active ingredient are both released from the dosage form at a substantially constant rate upon contacting of the dosage form with a liquid medium.

In certain other embodiments of this invention, upon contacting of the dosage form with a liquid medium, a time delay occurs prior to release of at least a portion of one or more active ingredients occurs followed by sustained release of the delayed release active ingredient or ingredients. In such embodiments, the time delay is provided by the dissolution of all or a portion of the molded matrix, and the subsequent sustained release is provided by one or more coatings on the particles of active ingredient. In such embodiments, the molded matrix preferably comprises a release modifying excipient selected from pH-dependent polymers. In such embodiments, the particle coating preferably comprises a release modifying excipient which may be selected from combinations of pore formers and insoluble edible materials; swellable erodible hydrophilic materials; pH-dependent polymers; and combinations thereof.

In another particular embodiment of this invention, the dosage form comprises first and second active ingredients which may be the same or different, and upon contacting of the dosage form with a liquid medium, sustained release of the first active ingredient occurs, followed by sustained release of the second active ingredient. In such embodiments, the sustained release of first active ingredient is provided by the controlled dissolution of all or a portion of the molded matrix, and the subsequent sustained release of the second active ingredient is provided by one or more coatings on the particles of active ingredient. In such embodiments, the molded matrix preferably comprises a release modifying excipient selected from swellable erodible hydrophilic materials, pH-dependent polymers, insoluble edible materials, and combinations thereof. In such embodiments, the particle coating preferably comprises a release modifying excipient which may be selected from combinations of pore formers and insoluble edible materials; swellable erodible hydrophilic materials; pH-dependent polymers, and combinations thereof.

In another particularly preferred embodiment of this invention, the matrix comprises a first dose of active ingredient and the particles contained therein comprise a second dose of active ingredient which may be the same or different than the first active ingredient, and upon contacting of the dosage form with a liquid medium, immediate release of the first dose of active ingredient occurs, followed by a lag time, which is in turn followed by delayed release of the second dose active ingredient. In such embodiments, the matrix preferably comprises materials which exhibit rapid dissolution in gastro-intestinal fluids. For example the immediate release shell portion or portions may comprise readily soluble materials selected from water soluble or water swellable thermoplastic film formers, water soluble or water swellable thickeners, crystallizable and non-crystallizable carbohydrates. In certain such embodiments, suitable water soluble or water swellable thermoplastic film formers may be selected from water swellable cellulose derivatives, thermoplastic starches, polyalkalene glycols, polyalkalene oxides, and amorphous sugar glass, and combinations thereof. In certain other such embodiments, suitable film formers may be selected from film forming water soluble polymers such as for example water soluble vinyl polymers, water soluble polycarbohydrates, water swellable cellulose derivatives, and water soluble copolymers; film-forming proteins, and combinations thereof. In certain other such embodiments, suitable thickeners may be selected from gelling polymers or hydrocolloids; gelling starches, and crystallizable carbohydrates, and combinations thereof. In certain other such embodiments, suitable non-crystallizable carbohydrates may be selected from polydextrose, starch hydrolysates, and non-crystallizable sugar alcohols, and combinations thereof. In such embodiments, the immediate release matrix will preferably liberate the coated particles of delayed release active ingredient by being breached or dissolved within 30 minutes in 900 ml water or 0.1 N HCl, or phosphate buffer solution at 37° C. with stirring by a USP type 2 (Paddle method) at 50 or 100 rpm. In these embodiments, the time delay is provided by a coating on the particles containing the second dose of active ingredient. Preferably the delayed release particle coating comprises a release-modifying excipient selected from swellable erodible hydrophilic materials, and pH-dependent polymers, and combinations thereof.

In another particularly preferred embodiment of this invention, the matrix comprises a first dose of active ingredient and the particles contained therein comprise a second dose of active ingredient which may be the same or different than the first dose of active ingredient, and upon contacting of the dosage form with a liquid medium, immediate release of the first dose of active ingredient occurs followed by sustained release of the second dose of active ingredient. In such embodiments, the matrix preferably comprises materials which exhibit rapid dissolution in gastro-intestinal fluids. For example the immediate release shell portion or portions may comprise readily soluble materials selected from water soluble or water swellable thermoplastic film formers, water soluble or water swellable thickeners, crystallizable and non-crystallizable carbohydrates. In certain such embodiments, suitable water soluble or water swellable thermoplastic film formers may be selected from water swellable cellulose derivatives, thermoplastic starches, polyalkalene glycols, polyalkalene oxides, and amorphous sugar glass, and combinations thereof. In certain other such embodiments, suitable film formers may be selected from film forming water soluble polymers such as for example water soluble vinyl polymers, water soluble polycarbohydrates, water swellable cellulose derivatives, and water soluble copolymers; film-forming proteins, and combinations thereof. In certain other such embodiments, suitable thickeners may be selected from gelling polymers or hydrocolloids; gelling starches, and crystallizable carbohydrates. In certain other such embodiments, suitable non-crystallizable carbohydrates may be selected from polydextrose, starch hydrolysates, and non-crystallizable sugar alcohols. In such embodiments, the immediate release matrix will preferably liberate the coated particles of delayed release active ingredient by being breached or dissolved within 30 minutes in 900 ml water or 0.1 N HCl, or phosphate buffer solution at 37° C. with stirring by a USP type 2 (Paddle method) at 50 or 100 rpm. In these embodiments, the sustained release is provided by a coating on the particles containing the second dose of active ingredient. Preferably the sustained release particle coating comprises a release-modifying excipient which may be selected from combinations of pore formers and insoluble edible materials; swellable erodible hydrophilic materials; pH-dependent polymers.

Preferably the molded matrix of the present invention is made by injecting the flowable material through an orifice into a mold cavity, then solidifying the flowable material, according to the method set forth herein. In one such embodiment wherein the dosage form comprises particles, the orifice has a diameter greater than the diameter of the particles, e.g. from about 1000 to about 4000 microns, say about 2000 to about 3000 microns. In certain such embodiments the particles are introduced into the mold cavity in the form of a flowable slurry or suspension in the matrix material. The flowable slurry or suspension may be introduced under pressure through the orifice. In one embodiment, the mold assembly may be free of a valve at the injection point. In another embodiment, the mold assembly may comprise an elastomeric plug type valve which does not crush the particles upon closing.

Advantageously this method provides a versatile and cost-effective process for preparing the modified release molded matrix systems of the present invention. Advantageously, the method of the present invention may be carried out at relatively low processing temperatures, enabling the incorporation of low melting active ingredients, heat labile active ingredients, and coated particles into molded matrix dosage forms. Advantageously the combination of methods and materials of the present invention enable the incorporation of relatively high levels of active ingredient into the molded matrix dosage form, and enable the production of unique elegant dosage forms with transparent, semi-transparent, or translucent matrices.

This invention will be illustrated by the following examples, which are not meant to limit the invention in any way.

EXAMPLE 1

Dosage forms according to the invention comprising a molded matrix were prepared using the ingredients in Table A as follows:

TABLE A

| Tablet | Trade Name | Manufacturer | Weight % | Mg/Tablet |
|---|---|---|---|---|
| Verapamil HCL E. R. Pellets | Verelan PM 300 mg capsules | Schwarz Pharma, Inc., Gainesville, GA | 17.0 | 77 |
| Polyethylene Glycol 3350 | Carbowax ® | Union Carbide Corporation, Danbury, CT | 42.0 | 190 |
| Shellac Powder | Regular bleached shellac | Mantrose-Haeuser Company, Atteboro, MA | 10.0 | 45 |
| Croscarmellose Sodium | Ac-Di-Sol ® | FMC Corporation, Newark, DE | 21.0 | 95 |
| Pseudoephedrine Hydrochloride Crystal | | BASF PharmaChemikalien GmbH & Co., Ludwigshafen/Rhein. | 10.0 | 45 |

A beaker was submersed in a water bath (Ret digi-visc; Antal-Direct, Wayne, Pa.) where the water temperature was set at 70° C. Polyethylene glycol (PEG) 3350 was added to the beaker and was mixed with a spatula until all PEG was melted. Shellac powder, which was screened through a #40 mesh screen, was added to the molten PEG and was mixed until all powder was dispersed. Croscarmellose sodium was added and the ingredients were mixed for 2 more minutes. Pseudoephedrine hydrochloride crystal was then added, followed by mixing for 2 more minutes. Verapamil HCl E. R. pellets, obtained by removing pellets from VERELAN PM 300 mg capsules, were added and the resulting mixture was mixed for 5 more minutes. 410 to 500 mg of the molten mixture was added to a round, concave lower punch and die unit (0.5000 inch diameter), which was manually joined with the upper punch to form a molded tablet dosage form. The molded tablet dosage form was ejected from the die.

Figure 2:
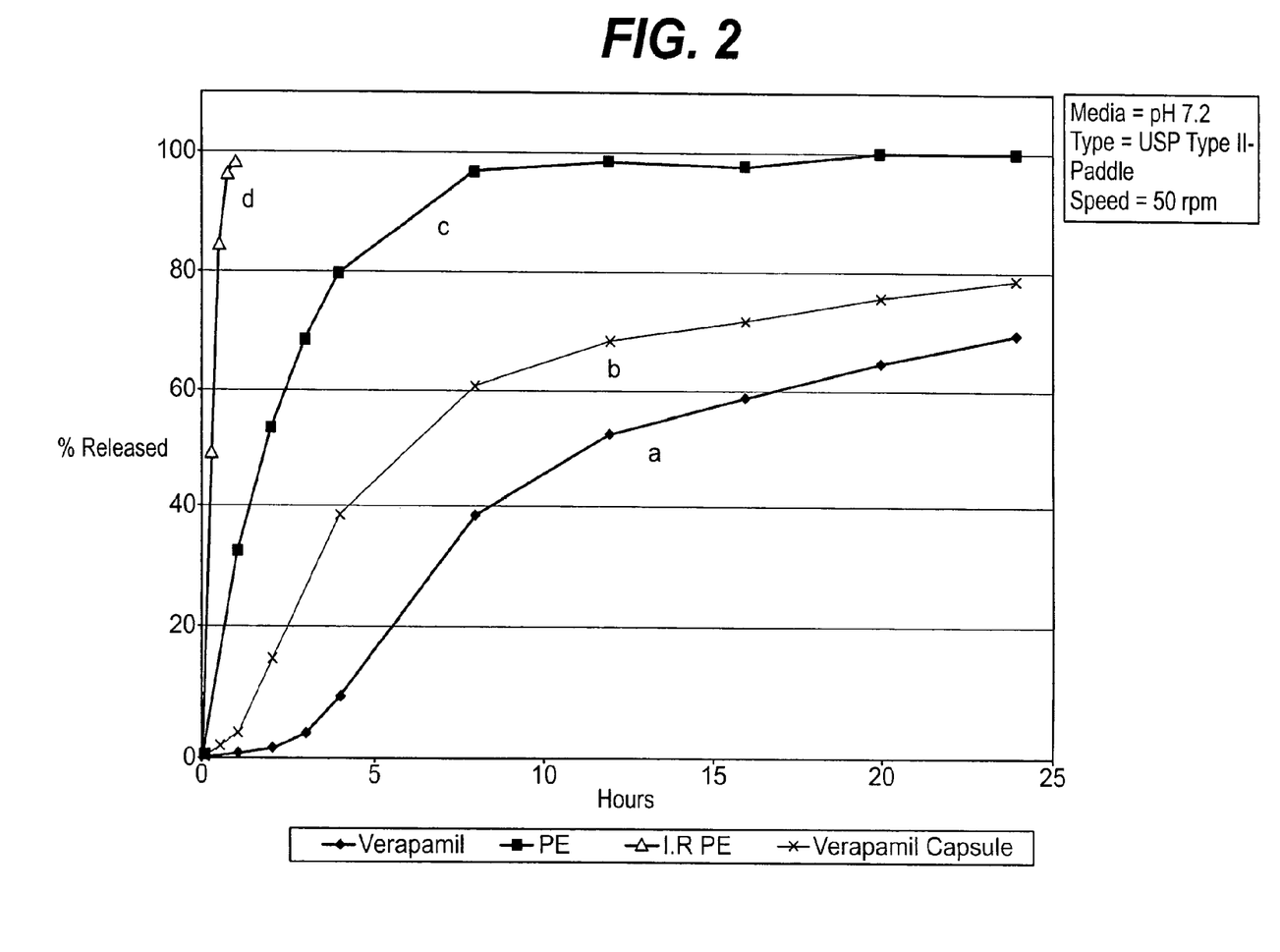
FIG. 2 depicts the % release of active ingredient vs. hours measured for the dosage form of Example 1.

FIG. 2 depicts the % release of active ingredient vs. hours for the dosage form of Example 1 and other dosage forms. More particularly this figure shows the dissolution rate of two different types of actives of the present invention as compared to two commercial products. Curve (a) shows the release rate of Verapamil HCL from the sustained release verapamil HCL pellets contained in this invention. The curve (b) was derived from the commercial sustained release dosage forms of Verelan PM 300 mg capsules (contains Verapamil HCL). Curve (c) shows the release rate of pseudoephedrine HCL from the matrix of this invention. The curve (d) was derived from the commercially immediate release dosage forms of Sudafed® tablet (containing pseudoephedrine HCL). All curves were derived using the following dissolution analysis: USP Type II apparatus (paddles, 50 RPM) in pH 7.2 phosphate buffer at 37° C. Samples were tested at 0.5, 1, 2, 4, 8, 12, 16, 20, and 24 hours for pseudoephedrine HCl, and Verapamil HCL. Dissolution samples were analyzed for pseudoephedrine HCl and Verapamil HCL versus a standard prepared at the theoretical concentration for 100% released of each compound. Samples were analyzed using a HPLC equipped with a Waters® 717 Autoinjector and a Waters® 486 UV detector set at a wavelength of 214 nm. The mobile phase was prepared using 55% acetonitrile and 45% 18 mM Potassium phosphate buffer. The injection volume was 50 μL with a run time of approximately 8 minutes and a pump flow of 2.0 ml/min. The column used was a Zorbax® 300-SCX (4.6 mm×25 cm).

EXAMPLE 2

Dosage forms according to the invention, comprising a molded matrix containing the ingredients listed in Table A above are made in a continuous process using a thermal cycle molding module as described on pages 27-51 of copending U.S. application Ser. No. 09/966,497. The ingredients are prepared as described in Example 1 and provided to the thermal cycle molding matrix in flowable form.

The thermal cycle molding module has the general configuration shown in FIG. 3 and pages 27-51 of copending U.S. application Ser. No. 09/966,497, which depicts a thermal cycle molding module 200 comprising a rotor 202 around which a plurality of mold units 204 are disposed. The thermal cycle molding module includes reservoir 206 (see FIG. 4) for holding the flowable material. In addition, the thermal cycle molding module is provided with a temperature control system for rapidly heating and cooling the mold units. FIGS. 55 and 56 of pending U.S. application Ser. No. 09/966,497 depict the temperature control system 600.

The thermal cycle molding module has the specific configuration shown in FIG. 26A of copending U.S. application Ser. No. 09/966,497. The thermal cycle molding module comprises center mold assemblies 212 and upper mold assemblies 214 as shown in FIG. 26C, which mate to form mold cavities. As rotor 202 rotates, the opposing center and upper mold assemblies close. The flowable material for the matrix, which is heated to a flowable state in reservoir 206, is injected into the resulting mold cavities. The temperature of the flowable material is then decreased, hardening the flowable material into a matrix. The mold assemblies open and eject the matrices.

Although this invention has been illustrated by reference to specific embodiments, it will be apparent to those skilled in the art that various changes and modifications may be made which clearly fall within the scope of this invention.

The invention claimed is:

1. A dosage form comprising:
   a molded matrix; and
   at least one active ingredient dispersed in the molded matrix,
   wherein the matrix comprises 10-100% of a thermal reversible carrier having a melting point of less than about 100 degrees C. selected from (a) polyethylene glycols having molecular weight from about 100 to about 20,000 Daltons; and (b) a release-modifying excipient comprising a combination of croscarmellose sodium and shellac, and
   wherein the matrix is capable of providing modified release of the active ingredient upon contacting the dosage form with a liquid medium.

2. A method for manufacturing a dosage form comprising a molded matrix and at least one active ingredient dispersed in the molded matrix comprising:
   injecting a matrix in flowable form into a molding chamber to form said dosage form,
   wherein the matrix comprises 10-100% of a thermal reversible carrier having a melting point of less than about 100 degrees C. selected from (a) polyethylene glycols having molecular weight from about 100 to about 20,000 Daltons; and (b) a release-modifying excipient selected from the group consisting of croscarmellose sodium, shellac and combinations thereof, and
   wherein the matrix is capable of providing modified release of the active ingredient upon contacting of the dosage form with a liquid medium.

3. A method for manufacturing a dosage form comprising a molded matrix and at least one active ingredient dispersed in the molded matrix at a level of more than about 20 weight percent comprising:
   injecting a matrix in flowable form into a molding chamber to form said dosage form,
   wherein the matrix comprises 10-100% of a material having a melting point of less than about 100 degrees C. selected from (a) polyethylene glycols having molecular weight from about 100 to about 20,000 Daltons; and (b) a release-modifying excipient comprising a combination of croscarmellose sodium and shellac, and
   wherein the matrix is capable of providing modified release of the active ingredient upon contacting of the dosage form with a liquid medium.

4. A method of claim 2, wherein said matrix comprises a plurality of particles, and at least a portion of the particles comprise at least one active ingredient.

5. A method of claim 3, wherein said matrix comprises a plurality of particles, and at least a portion of the particles comprise at least one active ingredient.

6. A method of claim 4, wherein at least a portion of the particles are coated with a coating capable of providing modified release of the active ingredient contained therein upon contacting of the dosage form with a liquid medium.

7. A method of claim 5, wherein at least a portion of the particles are coated with a coating capable of providing modified release of the active ingredient contained therein upon contacting of the dosage form with a liquid medium.

8. A method of claim 2, wherein the dosage form releases the active ingredient at a substantially constant rate.

9. A method of claim 2, wherein upon contacting of the dosage form with a liquid medium, a time delay occurs prior to release of at least a portion of the active ingredient.

10. A method of claim 9, wherein the portion of the active ingredient released after the time delay is released in a sustained manner.

11. A method of claim 2, wherein the dosage form additionally comprises a plurality of particles, the matrix comprises a first dose of active ingredient and at least a portion of the particles comprise a second dose of active ingredient which may be the same or different than the first active ingredient, and upon contacting of the dosage form with a liquid medium, immediate release of the first dose of active ingredient occurs followed by a lag time, followed by delayed release of the second dose of active ingredient.

12. A method of claim 3, wherein the dosage form additionally comprises a plurality of particles, the matrix comprises a first dose of active ingredient and at least a portion of the particles comprise a second dose of active ingredient which may be the same or different than the first active ingredient, and upon contacting of the dosage form with a liquid medium, immediate release of the first dose of active ingredient occurs followed by a lag time, followed by delayed release of the second dose of active ingredient.

13. A method of claim 2, wherein the thermal reversible carrier is from about 30 to about 70 weight percent of the matrix.

14. A method of claim 3, wherein the thermal reversible carrier is from about 30 to about 70 weight percent of the matrix.

* * * * *